US008316850B2

(12) United States Patent
Grilliot et al.

(10) Patent No.: US 8,316,850 B2
(45) Date of Patent: Nov. 27, 2012

(54) BREATHING APPARATUS WITH SENSOR

(75) Inventors: William L. Grilliot, West Milton, OH (US); Mary I. Grilliot, West Milton, OH (US); Allen Fritts, Durham, CT (US); Richard A. Bauer, Killingworth, CT (US)

(73) Assignee: Honeywell International Inc., Morristown, NJ (US)

( * ) Notice: Subject to any disclaimer, the term of this patent is extended or adjusted under 35 U.S.C. 154(b) by 993 days.

(21) Appl. No.: 12/242,262

(22) Filed: Sep. 30, 2008

(65) Prior Publication Data

US 2010/0078025 A1 Apr. 1, 2010

(51) Int. Cl.
*A61M 11/00* (2006.01)

(52) U.S. Cl. ......... 128/205.22; 128/201.25; 128/202.22; 128/204.26; 128/205.23

(58) Field of Classification Search ............. 128/201.25, 128/202.22, 204.26, 205.22, 205.23
See application file for complete search history.

(56) References Cited

U.S. PATENT DOCUMENTS

| | | | | |
|---|---|---|---|---|
| 5,572,991 | A | 11/1996 | Grilliot et al. | |
| 5,990,793 | A | 11/1999 | Bieback | |
| 6,118,382 | A * | 9/2000 | Hibbs et al. | 340/586 |
| 6,121,881 | A | 9/2000 | Bieback et al. | |
| 6,199,550 | B1 | 3/2001 | Wiesmann et al. | |
| 6,266,828 | B1 | 7/2001 | Corsini | |
| 6,328,031 | B1 | 12/2001 | Tischer et al. | |
| 6,417,774 | B1 | 7/2002 | Hibbs et al. | |
| 6,606,993 | B1 | 8/2003 | Wiesmann et al. | |
| 6,700,497 | B2 | 3/2004 | Hibbs et al. | |
| 6,720,878 | B2 | 4/2004 | Jumpertz | |
| 6,862,745 | B2 | 3/2005 | Grilliot et al. | |
| 6,930,608 | B2 | 8/2005 | Grajales et al. | |
| 6,934,571 | B2 | 8/2005 | Wiesmann et al. | |
| 6,995,665 | B2 | 2/2006 | Appelt et al. | |
| 7,034,677 | B2 | 4/2006 | Steinthal et al. | |
| 7,089,930 | B2 * | 8/2006 | Adams et al. | 128/201.27 |
| 7,091,852 | B2 | 8/2006 | Mason et al. | |
| 7,171,312 | B2 | 1/2007 | Steinthal et al. | |
| 7,380,551 | B2 * | 6/2008 | Alvey | 128/201.25 |
| 7,571,726 | B2 * | 8/2009 | Parker | 128/204.26 |
| 8,082,922 | B2 * | 12/2011 | McWilliams | 128/205.25 |
| 8,085,144 | B2 * | 12/2011 | Appelt et al. | 340/539.11 |
| 2004/0182394 | A1 | 9/2004 | Alvey et al. | |
| 2004/0182395 | A1 | 9/2004 | Brookman | |
| 2005/0001728 | A1 | 1/2005 | Appelt et al. | |
| 2006/0048777 | A1 | 3/2006 | Brookman | |
| 2006/0125623 | A1 * | 6/2006 | Appelt et al. | 340/521 |
| 2007/0183343 | A1 | 8/2007 | Grajales et al. | |
| 2008/0007396 | A1 | 1/2008 | Parkulo et al. | |
| 2008/0035145 | A1 * | 2/2008 | Adams et al. | 128/204.18 |

* cited by examiner

*Primary Examiner* — Steven Douglas
(74) *Attorney, Agent, or Firm* — Husch Blackwell

(57) ABSTRACT

A self-contained breathing apparatus or a respirator can be equipped with a sensor of ambient airborne conditions. A display unit can be carried by a face mask for the apparatus or respirator. Responsive to output signals from the sensor, the display unit can present an air quality indicator, or a breathability indicator to a user of the apparatus or respirator.

21 Claims, 3 Drawing Sheets

BREATHING APPARATUS WITH SENSOR

FIELD

The invention pertains to self-contained breathing apparatus (SCBA), or respirators. More particularly, the invention pertains to such units which include an air quality, or gas sensor or sensors to provide feedback to a user as to when the SCBA, or respirator should be used.

BACKGROUND

Various types of self-contained breathing apparatus are available for use by first responders such as fire fighters. Alternately respirators are available for use where an air filter will suffice. One such configuration is illustrated in U.S. Pat. No. 5,572,991 entitled, Air Flush System for a Firefighter's Garment which issued Nov. 12, 1996. Other configurations are illustrated in U.S. Pat. No. 6,328,031 entitled, Firefighting Hood and Face Mask Assembly which issued Dec. 11, 2001 and is incorporated herein by reference.

In all such situations, there is an on-going question as to whether the SCBA or the respirator continue to be needed. Unfortunately, at times, first responders will assume that the ambient air is safe to breathe, in the absence of any other information, and expose themselves to hostile or contaminated air.

There is thus a continuing need to provide such users with timely and accurate information as to local air quality. Preferably, such information can be provided using the type of equipment that they are used to and in a way which does not require them to make efforts to obtain such feedback.

DETAILED DESCRIPTION

Figure 1:
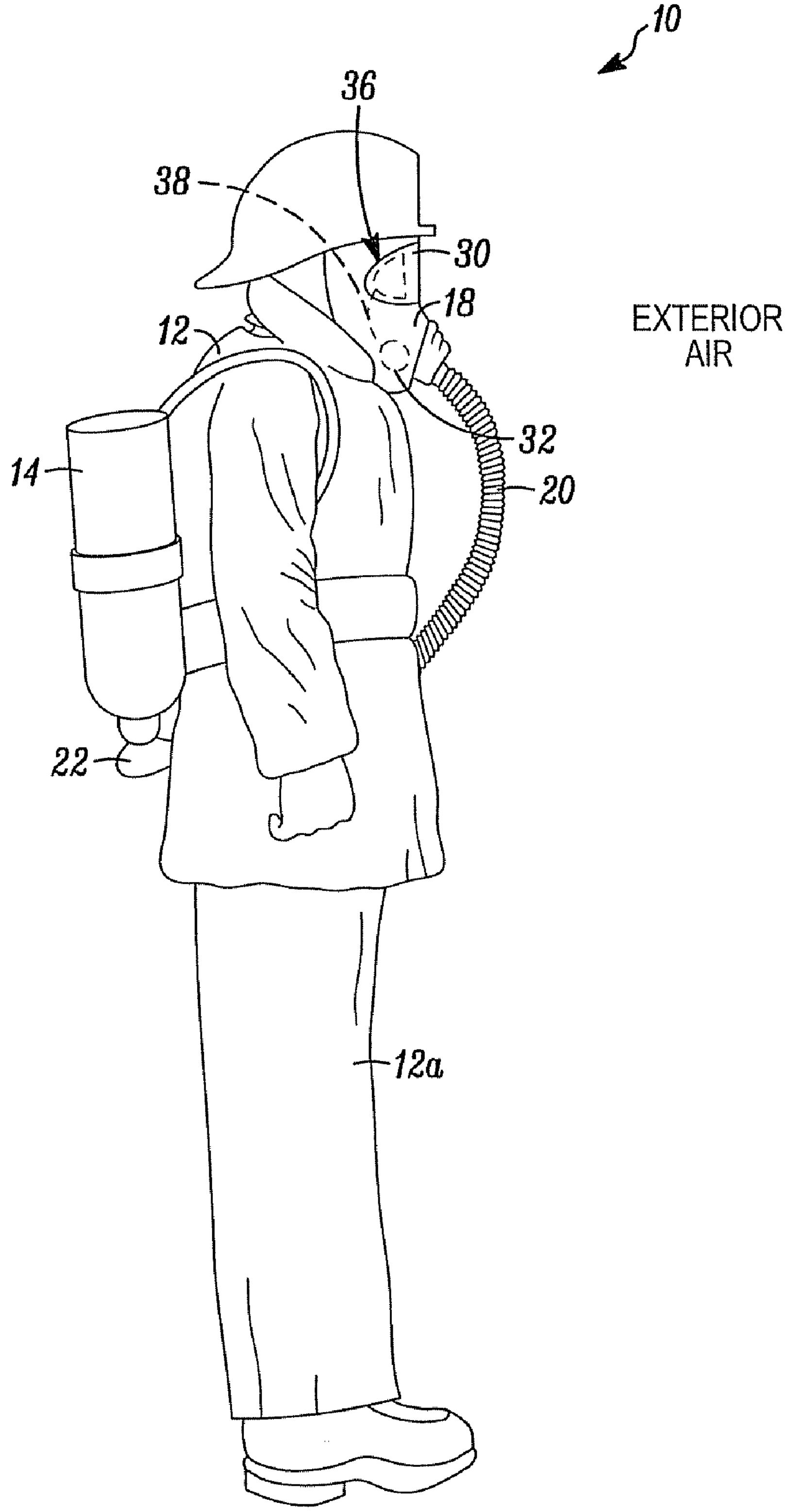
FIG. 1 is a side view of an apparatus which embodies the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In one aspect of the invention, either a SCBA or a respirator can be equipped with an air quality sensor and a heads-up display. The sensor or sensors can be located or carried anywhere on or in the vicinity of the SCBA or the respirator.

An air quality message can be visually presented for a user on a face mask which is part of the SCBA or the regulator. The message can be continually or intermittently presented to the user.

In another aspect of the invention, an air quality sensor can be carried on the face mask adjacent to the transparent face plate through which the user views the local region. Atmospheric quality evaluation circuitry can also be carried on the face mask, adjacent to the sensor.

A substantially transparent display can be located on the face plate. Alternately, a liquid crystal display or the like can be positioned on the face plate, visible to the user, but located so as not to interfere with over-all vision of the local region. Other types of visual output devices, such as light emitting diodes come within the spirit and scope of the invention and can also be used. Audible output devices can also be provided.

A variety of sensor types come within the spirit and scope of the invention. These include oxygen, carbon monoxide, or, carbon dioxide sensors, sensors of other dangerous or explosive gases, all without limitation. Devices which sense multiple different gases can also be used. Additionally, a temperature sensor can be provided in combination with the gas sensor(s) to provide feedback as to ambient temperatures.

FIG. 1 illustrates an apparatus 10 in accordance with the invention. The apparatus 10 includes a firefighter's protective outfit which includes a coat 12 and pants 12*a*. An illustrated SCBA includes a tank 14 of compressed breathable air coupled to a facemask 18 via a hose 20 and a regulator/valve 22. Hose 20 in combination with the regulator/valve 22 can convey breathable air to the user.

Figure 2:
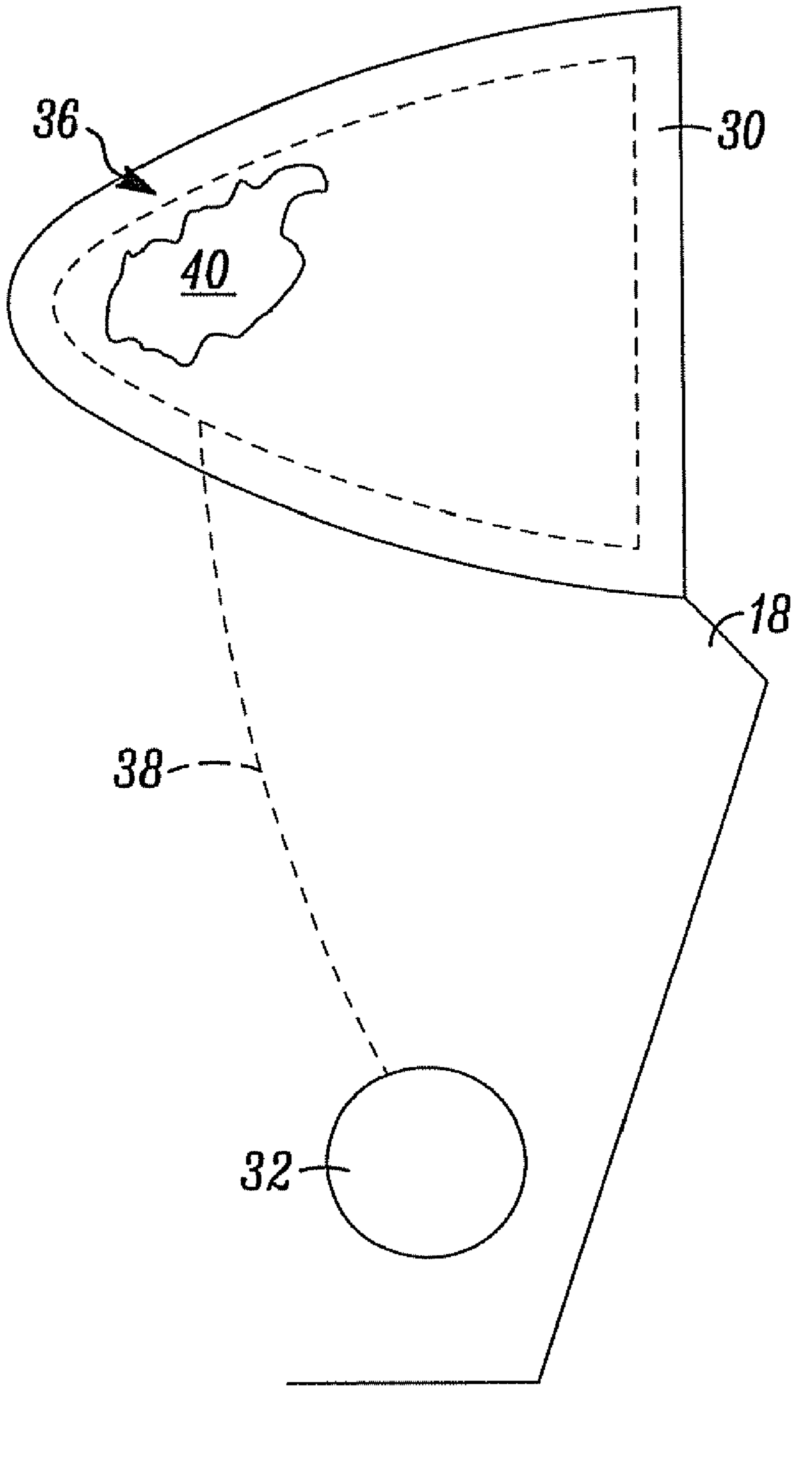
FIG. 2 is an enlarged partial view of a portion of the apparatus of FIG. 1.

Face mask 18 includes a transparent plastic face plate 30. As best seen in FIG. 2, mask 18 also carries a sensor of airborne gas or particulate matter 32 coupled to a heads-up type display 36 via conductors 38, shown in phantom in FIG. 1, 2.

As noted above, the sensor 32 can be selected from a variety of gas sensors, or sensors of airborne particulate matter such as smoke, and may be readily replaceable depending on the environment into which the first responder or fire fighter is operating. The exact details of such sensors are not limitations of the invention.

As illustrated in FIG. 2, air quality indicia 40 can be presented on the display 36. Representative indicia 40 could alphanumeric text that could display a message, such as AIR OK, or, DANGER, USE SCBA. Alternately, instead of a message, a symbol of acceptable quality, or a different symbol of danger can be displayed, all without limitation. Multiple messages or symbols, or both can be displayed as useful or appropriate.

Figure 3:
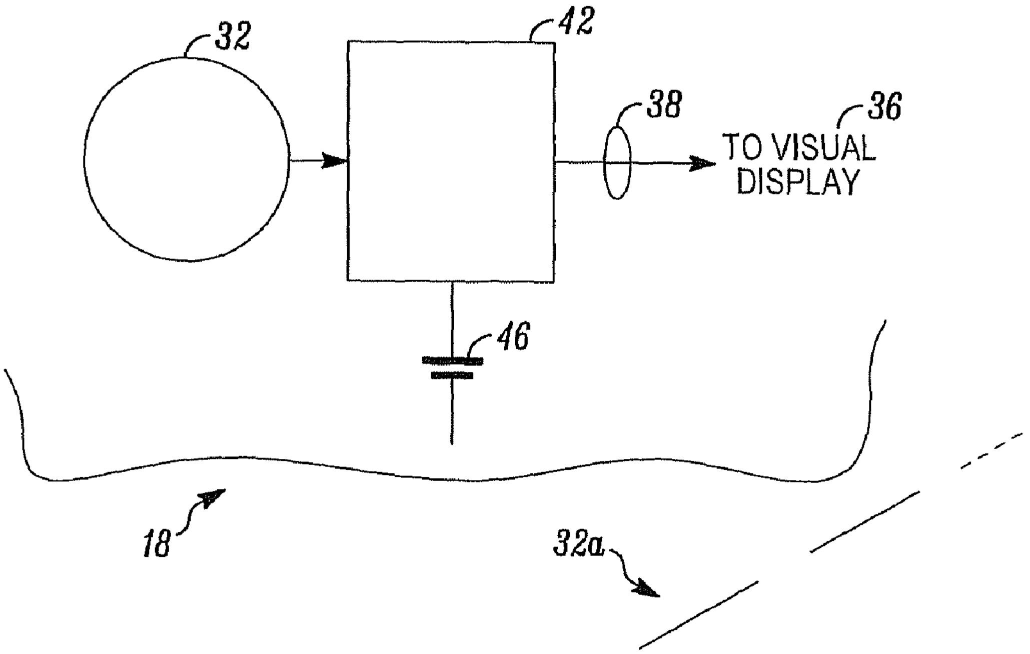
FIG. 3 is a block diagram illustrating additional details of the apparatus of FIG. 1.

FIG. 3 is a block diagram which illustrates sensor 32 coupled to control and evaluation circuits 42. The circuits 42 determine the acceptability of the ambient air outside of the face mask 18. As noted above, sensor 32 could be selected from a plurality of sensors 32*a* and could be field replaceable. Such replaceable units could couple their identity to circuits 42 for purposes of carrying out the appropriate quality evaluation. A temperature sensor could also be carried in the vicinity of sensor 32 and coupled to the control circuits 42 so as to provide feedback on the display as to local temperatures.

Output signals from circuits 42 can be coupled to the visual display 36 via the conductors 38. Power can be supplied by a replaceable battery 46. An audible output device, such as a beeper or horn could also be carried by the mask 18 and coupled to the control circuits 42 to provide an audible warning to a user.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A breathing unit comprising:

a tank for a breathable gas;

a user's face mask, the face mask has a transparent portion which carries a transparent visual display integrally incorporated thereon, the visual display presenting an electrically generated visual image;

a hose connecting the tank to the face mask;

control and evaluation circuits which provides an output indicative of an airborne condition sensed by one of a plurality of field replaceable sensors including an oxygen sensor, a carbon monoxide sensor, a carbon monoxide sensor, a sensor of explosive gases and a smoke particulate sensor; and a sensor coupled to the control and evaluation circuits, the sensor is selected from the plurality of field replaceable sensors depending upon the environment in which the breathing unit is used, the selected sensor couples its identity to the control and evaluation circuits for purposes of carrying out the appropriate quality evaluation of the sensed airborne condition, the output from the control and evaluation circuits is coupled to the display so as to continually provide the visual image indicative of the sensed concentration airborne condition on the transparent portion of the face mask.

2. A unit as in claim 1 where the detector includes a gas sensor coupled to control circuits.

3. A unit as in claim 2 with the control circuits coupled to the display.

4. A unit as in claim 3 where the control circuits evaluate at least one characteristic of ambient air outside of the face mask.

5. A unit as in claim 4 which includes an audible output device coupled to the control circuits.

6. A unit as in claim 4 where the visual display comprises a heads-up display.

7. A unit as in claim 6 where the display presents visual indicia of breathability of exterior air.

8. A unit as in claim 6 where display provides a visual indicator of a dangerous concentration of a sensed gas.

9. A unit as in claim 2 where the sensor can be selected from a plurality of sensors of different airborne gases or particulate matter.

10. A breathing unit comprising:

a face mask having a breathable air inflow port;

a transparent face plate carried by the mask and at least one of a visual display carried at least in part on the face plate, or an audible output device carried by the face mask, the visual display presenting an electrically generated visual image;

control and evaluation circuits responsive to an ambient gas sensed by one of a plurality of field replaceable sensors including an oxygen sensor, a carbon monoxide sensor, a carbon monoxide sensor, a sensor of explosive gases and a smoke particulate sensor; and a sensor coupled to the control and evaluation circuits, the sensor is selected from the plurality of field replaceable sensors depending upon the environment in which the breathing unit is used, the selected sensor couples its identity to the control and evaluation circuits for purposes of carrying out the appropriate quality evaluation of the sensed ambient gas with the control and evaluation circuits coupled to at least one of the display or the audible output device so as to provide at least one of a continuous visual indicator of the sensed ambient gas on the display of the face plate, or an audible indicator of gas concentration from the face mask.

11. A unit as in claim 10 which includes gas concentration evaluation circuits coupled between the sensor and the display, or the audible output device.

12. A unit as in claim 11 where the concentration evaluation circuits control the display, or the audible output device to present at least one of a gas concentration, an air quality indicator, or a local temperature.

13. A unit as in claim 12 with at least one of a source of pressurized breathable air, or, an air filter coupled to the face mask.

14. A breathing unit comprising a face mask carrying a detector and control circuits and having a transparent face plate, the detector providing an output indicative of an airborn condition sensed by one of a plurality of field replaceable sensors including an oxygen sensor, a carbon monoxide sensor, a carbon monoxide sensor, a sensor of explosive gases and a smoke particulate sensor, the face plate having a transparent visual display integrally incorporated thereon, a sensor coupled to the control circuits, the sensor is selected from the plurality of field replaceable sensors depending upon the environment in which the breathing unit is used, the selected sensor couples its identity to the control circuits for purposes of carrying out the appropriate quality evaluation of the sensed airborne condition, the control circuits electrically coupling the detector to the visual display within the face mask, the visual display presenting an electrically generated visual image, the visual image being continually indicative of the sensed airborn condition.

15. A unit as in claim 14 where the control circuits include a gas concentration evaluation circuit coupled between the sensor and the display.

16. A unit as in claim 14 where the visual image is displayed continually on the visual display.

17. A unit as in claim 14 where the visual display comprises a heads-up display.

18. A unit as in claim 14 where the display presents visual indicia of breathability of exterior air.

19. A unit as in claim 14 where display provides a visual indicator of a dangerous concentration of a sensed gas.

20. A unit as in claim 14 which includes a tank for a breathable gas.

21. A unit as in claim 20 which includes a hose connecting the tank to the face mask via a breathable air inflow port.

* * * * *